(12) United States Patent
Saettone et al.

(10) Patent No.: US 12,415,900 B2
(45) Date of Patent: Sep. 16, 2025

(54) PROCESS FOR PRODUCING POROUS PARTICLES OF A POLYHYDROXYALKANOATE (PHA), POROUS PARTICLES OBTAINABLE FROM SAID PROCESS AND COSMETIC COMPOSITIONS COMPRISING THE SAME

(71) Applicant: BIO-ON S.P.A., San Giorgio di Piano (IT)

(72) Inventors: Paolo Saettone, San Giorgio di Piano (IT); Antonino Ferraro, San Giorgio di Piano (IT); Lina Cellante, San Giorgio di Piano (IT); Carla Condo', San Giorgio di Piano (IT); Veronica Cicognani, San Giorgio di Piano (IT); Mauro Comes Franchini, San Giorgio di Piano (IT)

(73) Assignee: BIO ON S.P.A., Turin (IT)

( * ) Notice: Subject to any disclaimer, the term of this patent is extended or adjusted under 35 U.S.C. 154(b) by 847 days.

(21) Appl. No.: 17/441,050

(22) PCT Filed: Mar. 13, 2020

(86) PCT No.: PCT/IB2020/052311
§ 371 (c)(1),
(2) Date: Sep. 20, 2021

(87) PCT Pub. No.: WO2020/188439
PCT Pub. Date: Sep. 24, 2020

(65) Prior Publication Data
US 2022/0220273 A1    Jul. 14, 2022

(30) Foreign Application Priority Data
Mar. 19, 2019    (IT) .................. 102019000003981

(51) Int. Cl.
| | | |
|---|---|---|
| *C08J 9/16* | (2006.01) | |
| *A61K 8/02* | (2006.01) | |
| *A61K 8/85* | (2006.01) | |
| *A61Q 19/00* | (2006.01) | |
| *C08J 9/08* | (2006.01) | |

(52) U.S. Cl.
CPC .............. *C08J 9/16* (2013.01); *A61K 8/0279* (2013.01); *A61K 8/85* (2013.01); *A61Q 19/00* (2013.01); *C08J 9/08* (2013.01); *A61K 2800/54* (2013.01); *A61K 2800/60* (2013.01); *C08J 2203/02* (2013.01); *C08J 2367/04* (2013.01)

(58) Field of Classification Search
CPC ...... A61K 8/0241; A61K 8/0279; A61K 8/85; A61K 2800/54; A61K 2800/60; A61Q 19/00; C08J 9/08; C08J 9/16; C08J 2203/02; C08J 2367/04
See application file for complete search history.

(56) References Cited

U.S. PATENT DOCUMENTS

| | | |
|---|---|---|
| 6,610,764 B1 | 8/2003 | Martin et al. |
| 8,956,835 B2 | 2/2015 | Nakas et al. |
| 2008/0226580 A1 | 9/2008 | Maeda et al. |
| 2011/0275729 A1 | 11/2011 | Scandola et al. |

FOREIGN PATENT DOCUMENTS

| | | | |
|---|---|---|---|
| CN | 105418944 A | 3/2016 | |
| ES | 2394953 T3 * | 2/2013 | ............. A61K 47/34 |
| WO | 9923146 A1 | 5/1999 | |
| WO | 2011045625 A1 | 4/2011 | |
| WO | 2015015315 A2 | 2/2015 | |
| WO | 2018178899 A1 | 10/2018 | |

OTHER PUBLICATIONS

"A Guidebook to Particle Size Analysis" published by Horiba Instruments Inc.—2019, available on https://www.horiba.com/fileadmin/uploads/Scientific/ eMag/PSA/Guidebook/pdf/PSA_Guidebook.pdf.
Arun S. Mujumdar "Handbook of Industrial Drying" by Arun S. Mujumdar, CRC Press, 4th Edition (2014), pp. 1-316.
International Search Report issued May 19, 2020 re: Application No. PCT/IB2020/052311, pp. 1-3, citing: U.S. Pat. No. 6,610,764 B1, CN 105 418 944 B, US 2011/275729 A1 and US 2008/226580 A1.
Written Opinion issued May 19, 2020 re: Application No. PCT/IB2020/052311, pp. 1-5, citing: U.S. Appl. No. 6,610,764 B1, CN 105 418 944 B, US 2011/275729 A1 and US 2008/226580 A1.

* cited by examiner

*Primary Examiner* — John M Cooney
(74) *Attorney, Agent, or Firm* — CANTOR COLBURN LLP (57) ABSTRACT

A process for producing porous particles of a polyhydroxyalkanoate (PHA) includes the following steps: providing a spray drying atomization chamber heated to an operating temperature comprised between 50° C. and 300° C.; providing an aqueous suspension having the PHA and an expanding agent which decomposes at the operating temperature of the atomization chamber, with the formation of at least one gaseous compound; and injecting the aqueous suspension into the atomization chamber provided at the operating temperature, so as to cause instantaneous evaporation of the aqueous suspension and decomposition of the expanding agent, with formation of the porous PHA particles. The particles obtained from said process can be used to obtain cosmetic compositions that are soft to the touch, with high oil absorbing capacities and high flow index, able to generate a uniform, filling effect for wrinkles and skin furrows, making the skin more glossy and compact.

6 Claims, 2 Drawing Sheets

PROCESS FOR PRODUCING POROUS PARTICLES OF A POLYHYDROXYALKANOATE (PHA), POROUS PARTICLES OBTAINABLE FROM SAID PROCESS AND COSMETIC COMPOSITIONS COMPRISING THE SAME

TECHNICAL FIELD

The present disclosure relates to a process for producing porous particles of a polyhydroxyalkanoate (PHA). In particular, the present disclosure relates to a process for producing porous particles of a polyhydroxyalkanoate (PHA) by means of atomization (spray drying); the porous particles obtainable by this process and a cosmetic composition comprising said particles.

BACKGROUND

Polymers represent a class of products that are widely used in cosmetics, in particular for the preparation of emulsions, creams and suspensions for skin use. For example, hydrophilic polymers are used in oil-in-water emulsions as rheological modifiers and thickeners, but also as stabilizers, emulsifiers and moisturizers.

When these polymers are used in the form of fine powders, another function they may perform is that of texturizing agents (also called skin feel enhancers), i.e. agents that improve the tactile sensation felt by the consumer during the application of the product on the skin. The function of these agents is in fact to make the feeling perceived by the consumer when applying the product more pleasant, by improving the flowability and spreadability of the product and reducing the sensation of greasiness on the skin, giving the consumer a sensation of a "rich" formulation more suited for its intended purpose. In other words, the texturizing agent must increase the consistency of the cosmetic product, guarantee excellent properties of flowability and guarantee reduced skin greasiness.

The texturizing agent to be included in the cosmetic formulation is chosen according to the type of cosmetic product to be made (hydrogel, lipogel, emulsion, etc.) and may be a polymeric compound, such as nylon, polymethylmethacrylate (PMMA), polyurethane, silicone, or an inorganic compound, such as silica, talc, boron nitride, borosilicate.

Patent application WO 2018/178899, in the name of the same Applicant, relates to the use, as texturizing agents in cosmetic products, of polyhydroxyalkanoates (PHA), which are added in the form of particles obtained by spray drying. Specifically, WO 2018/178899 describes a cosmetic composition comprising: from 70% by weight to 99.9% by weight of a cosmetically acceptable basic formulation comprising an oily phase; from 0.1% by weight to 30% by weight of at least a polyhydroxyalkanoate (PHA) in particle form with an average diameter (d50) between 0.1 μm and 100 μm; these percentages are expressed in relation to the overall weight of the composition. The PHA in particle form acts as a texturizing agent and provides consistency to the cosmetic composition and flowability properties during application, in addition to reducing the sensation of greasiness on the skin. The PHA particles in fact have the capacity to absorb oily substances, minimising the greasy effect. By absorbing the excess sebum produced by the skin they make the skin less shiny. The PHA particles also contribute to the so-called "soft focus" effect, that is they contribute creating a uniform, filling effect for wrinkles and skin furrows, making the skin more glossy and compact.

The Applicant has faced the problem of improving the capacity of the PHA particles to absorb oily substances in order to further reduce the unpleasant sensation of skin greasiness and guarantee a more evident "soft focus" effect, without negatively influencing the flowability of the product.

SUMMARY

The Applicant has now found that this problem, and other which are better illustrated herein, can be solved using a process for producing porous particles of a polyhydroxyalkanoate (PHA) by means of atomization (spray drying) in the presence of an expanding agent, as better defined herein.

According to a first aspect, the present disclosure therefore relates to a process for producing porous particles of a polyhydroxyalkanoate (PHA), which comprises:
  providing a spray drying atomization chamber heated to an operating temperature comprised between 50° C. and 300° C.;
  providing an aqueous suspension comprising the PHA and an expanding agent which decomposes at the operating temperature of the atomization chamber, with the formation of at least one gaseous compound;
  injecting the aqueous suspension into the atomization chamber provided at the operating temperature, so as to cause instantaneous evaporation of the aqueous suspension and decomposition of the expanding agent, with formation of the porous PHA particles.

In the context of the present description and the attached claims, "expanding agent" refers to a substance able to thermally decompose with the production of at least one gaseous substance, which causes formation of pores in the polymeric material.

Preferably, the operating temperature of the atomization chamber is between 100° C. and 200° C.

According to the aims of the present disclosure, the expanding agent is preferably a carbonate or bicarbonate of an alkali metal or alkaline earth metal or of ammonium. Even more preferably, the expanding agent is selected from: ammonium bicarbonate, ammonium carbonate, sodium bicarbonate, calcium carbonate, magnesium carbonate, or mixtures thereof. Ammonium bicarbonate is particularly preferred.

In the process according to the present disclosure, the PHA is preferably present in the aqueous suspension at a concentration comprised between 1% w/v and 50% w/v, more preferably between 15% w/v and 25% w/v, the % being expressed by weight with respect to the total volume of the suspension. The expanding agent is preferably present in the aqueous suspension at a concentration comprised between 0.5% w/v and 30% w/v, more preferably between 1% w/v and 25% w/v, the % being expressed by weight with respect to the total volume of the suspension.

As is known, the atomization by spray drying transforms a solid in suspension in a liquid medium, usually an aqueous medium, into a dry product in the form of particles with a controlled size distribution. Such process generally includes injecting the liquid suspension at high pressure into an atomization chamber and in particular into a distribution ring, which is provided with a plurality of nozzles from which the suspension exits in the form of micro-droplets. Such micro-droplets are hit by a jet of a hot gas (generally air or nitrogen) which causes almost instantaneous evaporation of the liquid, with formation of the dried particles that are collected on the bottom of the device. Further details are provided for example in the manual "Handbook of Industrial Drying" by Arun S. Mujumdar, CRC Press, 4th Edition (2014).

Figure 1A:
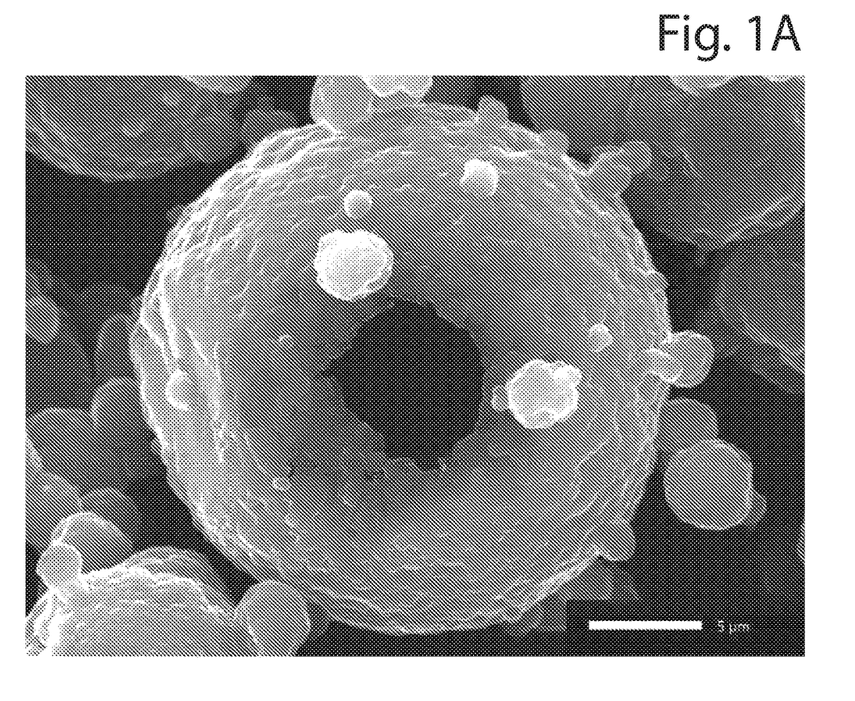
FIGS. 1A-1D show the PHB particles obtained according to the process described (microphotographs obtained by SEM electronic microscope).
Figure 1B:
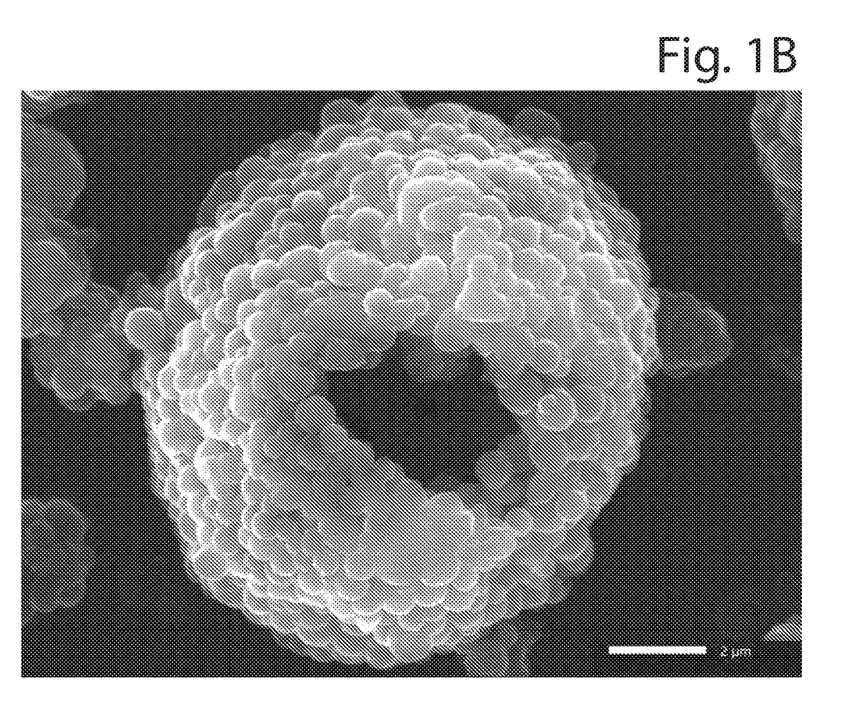
Figure 1C:
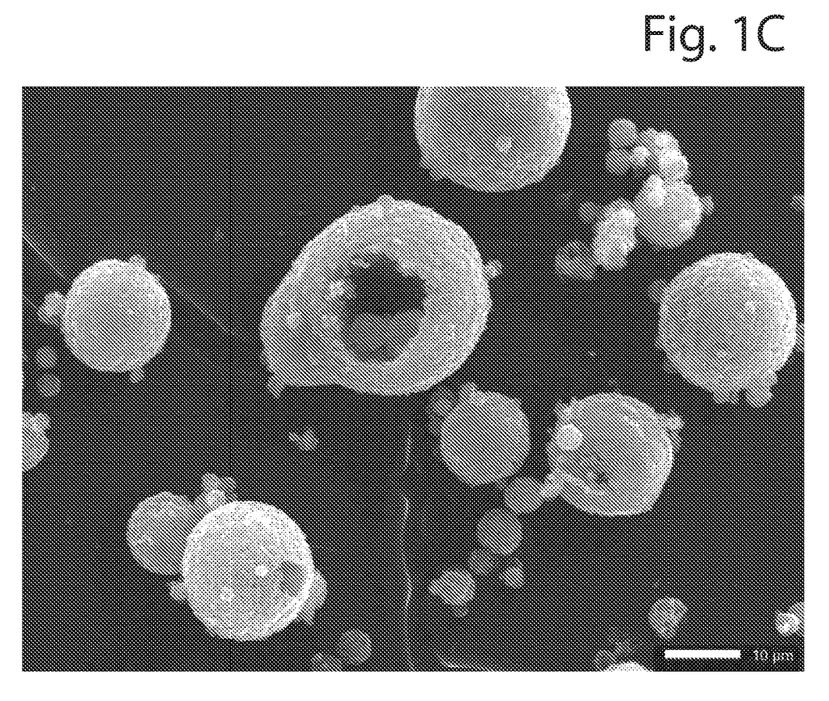
Figure 1D:
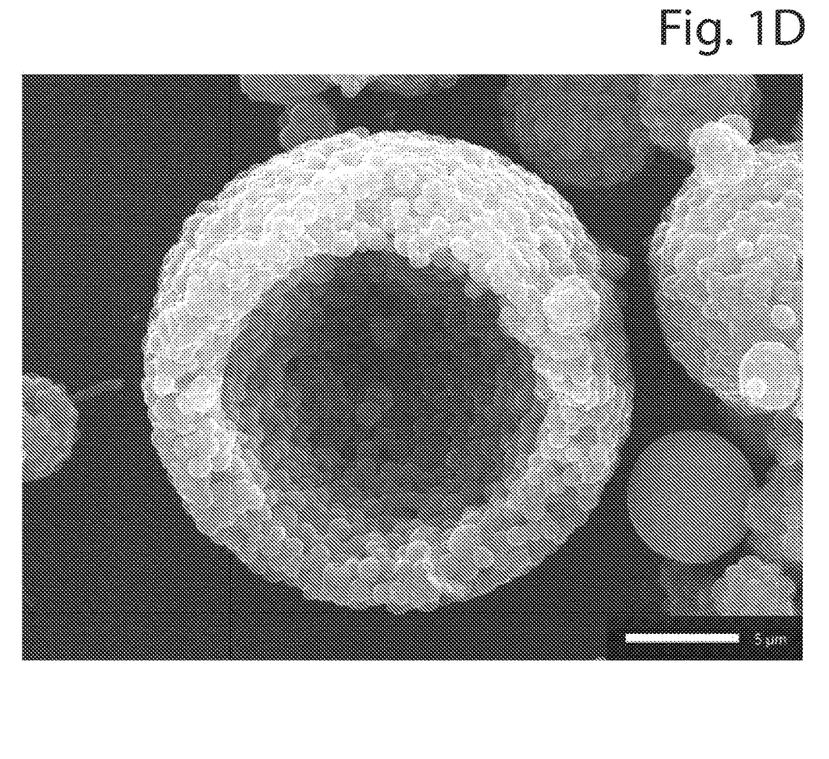

The particles produced by the process according to the present disclosure, as can be seen in FIGS. 1A-1D attached, have a porous structure, which, in some cases, may also present cavities or even through holes, forming substantially toroidal porous particles. This further improves the absorption capacities of the oily substances and modifies light reflecting properties, as better illustrated in the embodiments described below.

A second aspect of the present disclosure related to porous particles of a polyhydroxyalkanoate (PHA) obtainable by means of a process as described above.

As is known, polyhydroxyalkanoates (PHAs) are polymers produced by micro-organisms isolated from natural environments or even by genetically modified micro-organisms, and are characterized by high biodegradability. They are produced and accumulated by various species of bacteria under unfavourable growth conditions and in the presence of a source of excess carbon. PHAs are synthesized and accumulated by about 300 different microbial species, included in more than 90 types of Gram-positive and Gram-negative bacteria, such as for example *Bacillus, Rhodococcus, Rhodospirillum, Pseudomonas, Alcaligenes, Azotobacter, Rhizobium*.

In cells, PHA is stored in the form of microgranules, whose size and number per cell varies in different species. They appear as refractive inclusions under an electron microscope, with a diameter ranging from 0.2 to 0.7 μm.

For the purposes of the present disclosure, the PHA obtained from the microbial synthesis in the form of an aqueous suspension is subjected to an atomization process through a spray dryer.

From the process according to the present disclosure, it is possible to obtain porous PHA particles with an average diameter (d50) preferably between 1 μm and 150 μm, more preferably between 3 μm and 30 μm. The porous particles of PHA according to the present disclosure generally have low polydispersity of the particle size distribution, which can be calculated as "span", i.e. the ratio (d90-d10)/d50, where d90 is the diameter value below which 90% by weight of the particle population is found, d10 is the diameter value below which 10% by weight of the particles population is found, and d50 is the diameter value below which 50% by weight of the particle population is found (median value). Such ratio (span) preferably has a value from 1 to 3.

In the context of the present description and the attached claims, "average particle diameter" refers to, unless otherwise indicated, the diameter d50 (median value), i.e. the value of the diameter below which there is 50% by weight of the particle population (see "A Guidebook to Particle Size Analysis" published by Horiba Instruments Inc. 2016, available on https://www.horiba.com/fileadmin/uploads/Scientific/eMag/PSA/Guidebook/pdf/PSA Guidebook.pdf). It can be determined through a laser diffraction technique, according to ISO 13320:2009.

As for the PHA, this is preferably a polymer containing repeating units of formula:

$$—O—CHR_1—(CH_2)_n—CO—  \quad (I)$$

where:
R$_1$ is selected from: $C_1$-$C_{12}$ alkyls, $C_4$-$C_{16}$ cycloalkyls, $C_2$-$C_{12}$ alkenyls, optionally substituted with at least one group selected from: halogen (F, Cl, Br), —CN, —OH, —COOH, —OR, —COOR (R=$C_1$-$C_4$ alkyl, benzyl);

n is zero or an integer from 1 to 6, preferably 1 or 2.

Preferably, R$_1$ is methyl or ethyl, and n is 1 or 2.

The PHAs can either be homopolymers, copolymers or terpolymers. In the case of copolymers or terpolymers, they can consist of different repeating units of formula (I), or of at least one repetitive unit of formula (I) in combination with at least one repetitive unit deriving from comonomers that are able to copolymerize with hydroxyalkanoates, such as lactones or lactams. In the latter case, the repeating units of formula (I) are present in an amount equal to at least 10% in moles with respect to the total number of repeating units.

Particularly preferred repeating units of formula (I) are those deriving from: 3-hydroxybutyrate, 3-hydroxyvalerate, 3-hydroxyhexanate, 3-hydroxyoctanoate, 3-hydroxyundec-10-enoate, 4-hydroxyvalerate.

Particularly preferred PHAs are: poly-3-hydroxybutyrate (PHB), poly-3-hydroxyvalerate (PHV), poly-3-hydroxyhexanate (PHH), poly-3-hydroxyoctanoate (PHO), poly(3-hydroxybutyrate-co-3-hydroxyvalerate) (PHBV), poly(3-hydroxybutyrate-co-3-hydroxyhexanoate) (PHBH), poly(3-hydroxybutyrate-co-4-hydroxybutyrate), poly(3-hydroxyoctanoate-co-3-hydroxyundecen-10-enoate) (PHOU), poly(3-hydroxybutyrate-co-3-hydroxyvalerate-co-4-hydroxyvalerate) (PHBVV), polyhydroxybutyrate-hydroxyvalerate copolymer, or mixtures thereof.

According to the purposes of the present disclosure, the PHA is preferably a homopolymer, copolymer or terpolymer, more preferably a homopolymer, even more preferably a polyhydroxybutyrate (PHB).

Preferably, the PHA has a weight average molecular weight ($M_w$) that may vary from 10,000 to 1,000,000 Da.

With regard to the production of PHAs, this is preferably obtained from the microbial fermentation of an organic substrate (for example carbohydrates or other fermentable substrates, such as glycerol) using a strain of microorganisms capable of producing PHAs, and the subsequent recovery of the PHAs from the cell mass. For further details, reference is made, for example, to patent applications WO 99/23146, WO 2011/045625 and WO 2015/015315. Suitable substrates for the production of PHAs by fermentation can be obtained in particular from the processing of plants, for example juices, molasses, pulps from the processing of sugar beet, sugar cane. These substrates generally contain, in addition to sucrose and other carbohydrates, organic growth factors, nitrogen, phosphorus and/or other minerals which are useful as nutrients for cell growth. An alternative is glycerol, a low-cost organic carbon source, as it is a by-product of biodiesel production, which may also be used in a mixture with levulinic acid (see, for example, U.S. Pat. No. 8,956,835 B2).

According to a preferred embodiment of the present disclosure, the particles produced by the process according to the present disclosure have a bulk density value, measured by means of the method described in "European Pharmacopoeia 7.0-2.9.34", comprised between 0.1 g/ml and 0.5 g/ml, preferably between 0.2 g/ml and 0.4 g/ml.

The bulk density of a sample in the form of particles is the ratio between the non-compressed sample mass and its volume, which also includes the volume of the empty space between the particles. The bulk density therefore depends on the actual density of the product and the degree of packing of the particles constituting the sample. The bulk density is expressed in grams per millilitre (g/ml) and is measured at ambient temperature (20° C.)

Preferably, the particles according to the present disclosure have a value of tapped density, measured by means of the method described in "European Pharmacopoeia 7.0-2.9.34", comprised between 5% and 15%, preferably between 9% and 11%.

As described in said method, the tapped density is the density measured after compacting the particles, obtained by tapping on a container containing a sample of particles. The measurement is taken at ambient temperature (20° C.)

As can be seen better in the examples given below, the particles produced by the process according to the present disclosure, advantageously, have tapped density and bulk density values that are significantly lower than similar particles that are substantially free of porosity and cavities. In practical terms, these values characterise volatile particles that are light to the touch with high flowability properties.

Furthermore, advantageously, according to a preferred embodiment of the present disclosure, the particles have an oil (linseed oil) absorption value, measured according to ISO 787-5:1980, preferably comprised between 1 ml/g and 4 ml/g, preferably between 1.2 ml/g and 2.2 ml/g, where ml/g is the amount of absorbed oil, expressed in ml, per gram of particles.

In cosmetics, a shiny skin that reflects the light is perceived as unpleasant as it is an indicator of greasy or oily (hyperseborrheic) skin. The capacity of the particles produced by the process according to the present disclosure of absorbing oily substances may, advantageously, be used to remove excess skin sebum, for example in skin cleansing products, by means of the combined mechanical action of the hand and the particles, or in cosmetic products (make-up) in which the sebum-absorbing capacity is used to guarantee a mattifying effect even in the presence of sebum and/or sweat.

Therefore, the determination of the oil (linseed oil) absorption value of the particles is generally required to estimate the potential sebum-absorbing effect of the product once it is spread on the skin.

The appearance of skin wrinkles is the most evident sign of the skin ageing process. The wrinkle is defined as a line, slight furrow or fold in the skin which becomes thinner in that point. Typically, wrinkles appear in different areas of the face: beneath the eyes, on the forehead, around the lips, etc.

Advantageously, the particles according to the present disclosure have a softening/filling effect when applied to the skin.

The first evident effect is that of filling the empty space. To better understand the optical properties associated to the particles of the present disclosure, let us suppose that an incident light (with an angle of incidence of, for example, 30°) hits the wrinkle not from the front but from the side: in this way, an edge of the wrinkle will remain in shadow, while the other will be clearly visible. The morphology of the particles will not permit the direct reflection of the light, but will scatter it in different directions, making the cone of light that the profile of the illuminated edge would inevitably produce invisible. Furthermore, the refractive index (IR) of the PHA is similar to that of the stratum corneum of the skin (IR=1.55), and this similarity means that the light refracted by the particles has a colour similar to that of the skin.

According to another aspect, the present disclosure relates to a cosmetic composition comprising porous particles of a polyhydroxyalkanoate (PHA) obtainable by means of a process as described above, and a cosmetically acceptable basic formulation.

Preferably, the cosmetically acceptable basic formulation comprises an oily phase, which is preferably present in a quantity of between 50% by weight and 100% by weight, more preferably between 70% by weight and 90% by weight, in relation to the weight of the cosmetically acceptable basic formulation.

Preferably, the oily phase generally comprises at least a fatty substance of plant, mineral or synthetic origin, which may be in liquid form (oils) or solid form (waxes) at ambient temperature (25° C.). Preferably, the oily phase comprises at least a non-volatile oil which provides an emollient effect for the skin. "Non-volatile oil" refers to a liquid fatty substance at ambient temperature (25° C.) which is able to remain on the skin after application for at least one hour, with in particular a vapour pressure at 25° C. and an atmospheric pressure less than or equal to 0.01 mmHg (1.33 Pa).

Generally, the oily phase is composed of hydrocarbon-, silicone-based or fluorinated compounds, particularly fatty acids, fatty alcohols, fatty acid esters, for example: cetearyl isononanoate, isotridecyl isononanoate, isostearyl isostearate, isopropyl isostearate, isopropyl myristate, isopropyl palmitate, butyl stearate, ethyl laurate, isononyl isononanoate, 2-ethylhexyl palmitate, 2-hexyldecyl laurate, 2-hexadecyl palmitate, 2-hexadecyl myristate or lactate, (2-ethylhexyl)succinate, diisostearyl malate, glycerol or triglycerol triisostearate, tocopheryl acetate, myristic acid, palmitic acid, stearic acid, behenic acid, oleic acid, linoleic acid, linolenic acid, isostearic acid, dimethicone, triglycerids decanoic/capric acid, oleyl alcohol, avocado oil, camelia oil, castor seed oil, macadamia nut oil, turtle oil, mink oil, soy oil, grapeseed oil, sesame oil, corn oil, rapeseed oil, sunflower oil, cotton seed oil, jojoba oil, peanut oil, olive oil, and their mixtures.

Mineral oils may also be used, even though these are less preferable in terms of environmental sustainability, such as light paraffins, squalene, petroleum gel, and their mixtures.

The oily phase may also comprise at least a volatile oil, that is a liquid fatty substance at ambient temperature (25° C.) which evaporates after application on the skin in less than one hour, having in particular a vapour pressure at 25° C. and atmospheric pressure of more than 0.01 mmHg (1.33 Pa) and generally less than or equal to 300 mmHg (40,000 Pa). Volatile oils may be for example silicone oils, which contribute to reducing the greasy effect of the fatty phase.

The cosmetically acceptable basic formulation may also comprise an aqueous phase, which is preferably present in a quantity of no more than 50% by weight, more preferably between 10% by weight and 30% by weight, in relation to the weight of the basic formulation. In addition to water, the aqueous phase may comprise products that are miscible in water, such as: primary and secondary alcohols (for example ethanol or isopropanol); polyols (for example glycerol, propylene glycol, butylene glycol, dipropylene glycol, diethylene glycol); glycol ethers (for example mono-, di- or tri-propylene glycol); mono-, di- or tri-ethylene glycol-C1-C4-alkyl ethers; carboxylic acids (for example benzoic acid); or their mixtures.

The aqueous phase may also comprise stabilizers, such as sodium chloride, aluminium oxide, magnesium dichloride, magnesium sulphate, zinc dichloride.

The aqueous phase may also comprise other products compatible with the aqueous phase, such as gelling agents, filming agents, thickeners, surfactants, and mixtures thereof.

The cosmetically acceptable basic formulation may also comprise other products typically used in cosmetic products, with a merely formulation function, which depend on the specific product in preparation, such as:

anionic, cationic, amphoteric or non-ionic surfactants, which facilitate dispersion of the aqueous phase in the oily phase or vice versa, to obtain a stable water-in-oil or oil-in-water emulsion;

preservatives, for example parabens and phenoxyethanol;

thickeners, such as rubbers and waxes, for example hydroxypropyl guar, carrageenan, hydroxyethyl cellulose, xantham gum, guar gum, beeswax, candelilla wax, ceresin;

chelating agents, for example ethylenediaminetetraacetic acid (EDTA);

colouring agents and pigments.

The cosmetically acceptable basic formulation may also comprise at least an active ingredient with a specific biological activity, for example:

hydrating agents and nutrients, for example amino acids or proteins (glycine, alanine, threonine, citrulline, serine, caseine, elastine), alpha-hydroxy acids, sugars (lactose, mannose, fructose, galactose, pectin), vitamins (for example vitamin A, D or E);

astringent agents, for example aluminium salts;

antiseptic agents, for example trichlorocarbanilide (TCC), dichlorophen, bromo chlorophenol, essential oils;

anti-inflammation and anti-irritation agents, for example bisabolol, dipotassium glycyrrhizinate, rosemary extracts;

antimicrobial, bacteriostatic agents, bactericides, fungistatics or fungicides, for example zinc salts;

anticellulite agents, for example caffeine or its derivatives, escin, lecithin, carnitine;

anti-seborrheics, for example iminodibenzyl or fluorene derivatives, glucuronic acid, niacinamides, salicylic acid;

keratolytic or desquamating agents, for example alpha-hydroxy acids, beta-hydroxy acids, alpha-keto acids, beta-keto acids, retinoids;

opacifiers, for example clays, kaolins, anti-lipase agents, ethyl lactate;

anti-wrinkle agents, for example proteins and their hydrolysates, collagen, hyaluronic acid;

anti-oxidants, for example butylated hydroxytoluene (BHT), butylated hydroxyanisole (BHA), propyl gallate, octyl gallate, carotenoids, including beta-carotene, lycopene or canthaxanthin, ubiquinone, vitamin E, vitamin C;

anti-free radical agents, for example vitamin E, caffeine, mannitol, enzymes;

sun filters, including agents that absorb UV-A and/or UV-B rays, pigments or nano-pigments;

vasoconstrictors;

microcirculation reactivators;

decongestants;

deodorants, perfumes and antiperspirants;

depilatories, for example thioglycol and thiolactic acid salts.

The cosmetic composition according to the present disclosure can be used to produce a wide range of cosmetic products, and in particular:

facial make-up products, such as foundation, eye shadow, mascara, eye-liner, lipstick;

face and body care products, such as creams, milks, lotions, detergents, deodorants, antiperspirants, shaving products, depilatories;

hair care products, such as shampoo, gel, anti-dandruff products, products to control hair loss, hair dyeing and bleaching products;

perfumery products, particularly milks and creams.

DETAILED DESCRIPTION OF THE DISCLOSURE

The following examples of embodiment are provided for the sole purpose of illustrating the present disclosure and are not to be understood to limit the scope of protection defined by the appended claims.

Example 1: Process for Producing Porous Particles of PHB by Means of Atomization (Spray Drying)

The atomization chamber of a spray dryer was heated to a temperature of 200° C. An aqueous suspension of PHB at 20% w/v was prepared, the % being expressed by weight in relation to the total volume of the suspension. Ammonium bicarbonate was added to the suspension in a quantity equal to 10% w/v, the % being expressed by weight in relation to the total volume of the suspension. Ammonium bicarbonate decomposes at 35° C., leading to the formation of carbon dioxide and ammonia, it therefore acts as an expanding agent in accordance with the present disclosure.

The PHB suspension containing ammonium bicarbonate was nebulized inside the atomization chamber through an injection nozzle. The nebulization obtained drops of PHB suspension. The drops were hit by an air flow with a temperature of 200° C., which assured the instantaneous evaporation of the water present in the suspension and the decomposition of the ammonium bicarbonate, with the formation of carbon dioxide and ammonia. The development of these gases led to the formation of a porous and hollow structure of the PHB particles.

Example 2: Characterisation of the Particles in Example 1

Apparent Density.

The analysis to determine the bulk density of the particles in Example 1 was performed three times. The particles in Example 1 were sieved using a sieve with 1.0 mm mesh. 50 g of particles in Example 1 were poured slowly into a 250 mL graduated glass cylinder (tolerance±2 mL). The analysis was conducted following the indications of the "European Pharmacopoeia 7.0-2.9.34" method. Table 1 gives the average values of the three analyses conducted; the bulk density is expressed as grams of particles in millilitres of volume occupied by the particles (g/mL) and the bulk density values are expressed in relation to the average diameter (d50) of the particles analysed.

TABLE 1

| Average diameter (d50) | Apparent density (g/mL) |
| --- | --- |
| 5 μm | 0.220 |
| 10 μm | 0.280 |
| 20 μm | 0.340 |
| 30 μm | 0.380 |

Table 2 gives the bulk density values obtained by analysing samples of PHB particles obtained by spray drying according to the same procedure described in Example 1, but without any expanding agent (ammonium bicarbonate).

TABLE 2

| Average diameter (d50) | Apparent density (g/mL) |
|---|---|
| 5 μm | 0.240 |
| 10 μm | 0.310 |
| 20 μm | 0.380 |
| 30 μm | 0.410 |

Comparing the values of the two tables, it is clear how the particles obtained from the process according to the present disclosure are characterised by a lower bulk density.

Tapped Density.

The analysis to determine the tapped density of the particles in Example 1 was performed three times. The particles in Example 1 were sieved using a sieve with 1.0 mm mesh. 50 g of particles in Example 1 were poured slowly into a 250 mL graduated glass cylinder (tolerance±2 mL). The analysis was conducted following the indications of the "European Pharmacopoeia 7.0-2.9.34" method. Table 3 gives the average values of the three analyses conducted; the tapped density is expressed as a percentage obtained by the following formula $$\frac{100 \times (V_0 - V_f)}{V_0}$$

wherein $V_0$ corresponds to the initial volume occupied by the particles in the cylinder, $V_f$ is the volume of the particles after tapping the cylinder that contains them.

TABLE 3

| Average diameter (d50) | Tapped density (%) |
|---|---|
| 5 μm | 10.4 |
| 10 μm | 10.2 |
| 20 μm | 10.0 |
| 30 μm | 9.7 |

Table 4 gives the tapped density values obtained by analysing samples of PHB particles obtained by spray drying according to the same procedure described in Example 1, but without any expanding agent (ammonium bicarbonate).

TABLE 4

| Average diameter (d50) | Tapped density (%) |
|---|---|
| 5 μm | 11.3 |
| 10 μm | 10.5 |
| 20 μm | 10.2 |
| 30 μm | 9.7 |

Comparing the values of the two tables, it is clear how the particles obtained from the process according to the present disclosure are characterised by a lower tapped density.

Oil Absorption (Linseed Oil).

The analysis to determine the oil absorption value of the particles in Example 1 was conducted two times in accordance with standard ISO 787-5:1980.

The analysis was conducted on a concave glass support, of a circular shape and with a diameter of approximately 17 cm on which 1 g of the particles in Example 1 was weighed. Cyclically, 4/5 drops of linseed oil were added to the particles using a 10 mL burette (with a measurement error equal to 0.02 mL) to obtain a compact, smooth and non-sticky paste, without lumps or cracks. The procedure then continued adding 1 drop at a time of oil until the consistency required by the standard was reached. After each addition of oil, the particles were mixed carefully to allow the oil to be absorbed appropriately.

The oil absorption value was expressed in terms of millilitres of oil absorbed per gram of particles (mL/g). The results are given in Table 5.

TABLE 5

| Average diameter (d50) | Oil absorption (mL/g) |
|---|---|
| 5 μm | 1.57 |
| 10 μm | 1.73 |
| 20 μm | 1.73 |
| 30 μm | 1.66 |

Table 6 gives the linseed oil absorption values obtained by analysing samples of PHB particles obtained by spray drying according to the same procedure described in Example 1, but without any expanding agent (ammonium bicarbonate).

TABLE 6

| Average diameter (d50) | Oil absorption (mL/g) |
|---|---|
| 5 μm | 1.48 |
| 10 μm | 1.37 |
| 20 μm | 1.34 |
| 30 μm | 1.27 |

Comparing the values of the two tables, we can see a net increase in the oil absorption values by the particles obtained with the process according to the present invention compared to the non-porous and non-hollow particles of the same grain size (d50).

A similar analysis was also conducted to assess the absorption capacity of another oil, isopropyl myristate.

The oil absorption value was expressed in terms of millilitres of oil absorbed per gram of particles (mL/g). The results are given in Table 7.

TABLE 7

| Average diameter (d50) | Oil absorption (mL/g) |
|---|---|
| 5 μm | 1.35 |
| 10 μm | 1.65 |
| 20 μm | 1.69 |
| 30 μm | 1.77 |

Table 8 gives the isopropyl myristate absorption values obtained by analysing samples of PHB particles obtained by spray drying according to the same procedure described in Example 1, but without any expanding agent (ammonium bicarbonate).

TABLE 8

| Average diameter (d50) | Oil absorption (mL/g) |
|---|---|
| 5 μm | 1.35 |
| 10 μm | 1.30 |
| 20 μm | 1.29 |
| 30 μm | 1.21 |

Comparing the values of the two tables, we can see a net increase in the oil absorption values by the particles obtained with the process according to the present disclosure compared to the non-porous and non-hollow particles of the same grain size (d50).

Example 3: Cosmetic Composition Comprising the Particles in Example 1

Table 9 shows the cosmetically acceptable basic formulation used to produce the cosmetic composition. The quantities are expressed as % p/p, in relation to the total weight of the composition.

TABLE 9

| Excipients (% p/p) | |
|---|---|
| Water | 73.3 |
| Sepigel 305 | 0.5 |
| Montanov 68 | 5 |
| Lanol 99 | 20 |
| Benzyl alcohol | 1.2 |

After weighing, both the aqueous phase, composed of water and Sepigel 305, and the oily phase, composed of 99 and Montanov 68, were heated to a temperature of 80° C. Having reached the required temperature and once the substances reached the liquid state, the two phases were joined and homogenised using a turbo-emulsifier at 3200 rpm for 5 minutes. The emulsion obtained thus was allowed to cool slowly to a temperature of 40° C. Thereafter, benzyl alcohol (preservative) was added. The particles in Example 1 were added to this formulation in a quantity equal to 2% p/p, the % expressed in relation to the total weight of the cosmetic composition.

Example 4: Gloss Index of the Cosmetic Composition in Example 3

In cosmetics, the analysis for the determination of gloss index is used for the characterisation of cosmetic compositions comprising particles. According to its own chemical and physical characteristics, each particle may in fact interact differently to visible light radiation. The gloss index refers to the value obtained by using a glossmeter, an instrument that is able to determine light reflection, that is the light intensity defined within a restricted area around the angle of reflection, which is the same as incident light.

The gloss index is measured in accordance with standard BS EN ISO 2813:2014. A low index corresponds to a cosmetic composition that is able to cause the diffraction rather than the reflection of the light, thus contributing to creating a uniform and filling effect on wrinkles and skin furrows, making the skin more glossy and compact.

The gloss index was determined by measuring, with the glossmeter, a film of the cosmetic composition in Example 3 with a thickness of 150 µm, spread on a sheet of Byk Chart glossy paper (Byk-Gardner, Germany) using a film-applicator (Byk-Gardner, Germany). The analysis was carried out 2 hours after spreading the film on the sheet of paper. The glossmeter (Micro-TRI-gloss, Byk-Gardner, Germany) was set at an incidence angle firstly of 60° and then 85°. The gloss index value given in Table 10 is the average result of 5 measurements made on different points of the film, per different grain size (d50) of the particles. The gloss index was expressed as an average value with its standard deviation (STD) selecting the angle of incidence 60° for a first reading, and in the case of value lower than 10 GU (gloss unit), the measurement was repeated with an angle of incidence of 85°.

TABLE 10

| Cosmetic composition | d50 particles | 60° Average value | STD | 85° Average value | STD |
|---|---|---|---|---|---|
| Without particles | — | 6.5 | 0.8 | 18.3 | 1.3 |
| With particles | 5 µm | 5.8 | 0.6 | 13.8 | 2.2 |
| With particles | 10 µm | 5.6 | 0.1 | 8.0 | 0.8 |
| With particles | 20 µm | 5.4 | 0.1 | 4.0 | 1.1 |
| With particles | 30 µm | 5.0 | 0.1 | 3.8 | 0.7 |

Table 11 on the other hand gives the gloss index values obtained by analysing a cosmetic composition comprising particles of PHB free of porosity and cavities (therefore not obtained with the method according to the present disclosure).

TABLE 11

| Cosmetic composition | d50 particles | 60° Average value | STD | 85° Average value | STD |
|---|---|---|---|---|---|
| Without particles | — | 6.9 | 0.7 | 18.3 | 1.3 |
| With particles | 5 µm | 3.4 | 0.3 | 10.1 | 1.3 |
| With particles | 10 µm | 3.0 | 0.2 | 8.4 | 1.5 |
| With particles | 20 µm | 2.6 | 0.1 | 6.2 | 0.4 |
| With particles | 30 µm | 2.2 | 0.1 | 4.3 | 0.5 |

From the analysis of the results obtained at 60°, comparing the composition without particles with the composition in Example 3, a progressive reduction of the gloss index can be seen as the particle grain size (d50) increases.

In conclusion, the particles according to the present disclosure are used to obtain cosmetic compositions that are soft to the touch, with high oil absorbing capacities and high flow index, able to generate a uniform, filling effect for wrinkles and skin furrows, making the skin more glossy and compact.

The invention claimed is:

1. A process for producing porous particles of a polyhydroxyalkanoate (PHA), which comprises the following steps:
   providing a spray drying atomization chamber heated to an operating temperature comprised between 50° C. and 300° C.,
   providing an aqueous suspension comprising the PHA and an expanding agent which decomposes at the operating temperature of the atomization chamber, with formation of at least one gaseous compound, and
   injecting the aqueous suspension into the atomization chamber provided at the operating temperature, so as to cause instantaneous evaporation of the aqueous suspension and decomposition of the expanding agent, with formation of the porous PHA particles.

2. The process according to claim 1, wherein the expanding agent is a carbonate or bicarbonate of an alkali or alkaline earth metal or of ammonium.

3. The process according to claim 2, wherein the expanding agent is selected from: ammonium bicarbonate, ammonium carbonate, sodium bicarbonate, calcium carbonate, magnesium carbonate, or mixtures thereof.

4. The process according to claim 1, wherein the operating temperature of the atomization chamber is comprised between 100° C. and 200° C.

5. The process according to claim 1, wherein the PHA is present in the aqueous suspension at a concentration comprised between 1% w/v and 50% w/v, the % being expressed by weight with respect to the total volume of the suspension.

6. The process according to claim 1, wherein the expanding agent is present in the aqueous suspension at a concentration comprised between 0.5% w/v and 30% w/v, the % being expressed by weight with respect to the total volume of the suspension.

* * * * *

UNITED STATES PATENT AND TRADEMARK OFFICE
CERTIFICATE OF CORRECTION

| | | |
|---|---|---|
| PATENT NO. | : 12,415,900 B2 | Page 1 of 1 |
| APPLICATION NO. | : 17/441050 | |
| DATED | : September 16, 2025 | |
| INVENTOR(S) | : Paolo Saettone et al. | |

It is certified that error appears in the above-identified patent and that said Letters Patent is hereby corrected as shown below:

On the Title Page

Item (73), the name of the Assignee should read "BIO-ON S.P.A." and the address should read "San Giorgio di Piano (IT)".

Signed and Sealed this
Ninth Day of December, 2025

John A. Squires
*Director of the United States Patent and Trademark Office*